United States Patent [19]

Killough

[11] Patent Number: 5,098,662
[45] Date of Patent: Mar. 24, 1992

[54] MODULAR SOLVENT EXTRACTOR/CONCENTRATOR APPARATUS

[75] Inventor: Bruce A. Killough, Corning, N.Y.

[73] Assignee: Corning Incorporated, Corning, N.Y.

[21] Appl. No.: 566,216

[22] Filed: Aug. 10, 1990

[51] Int. Cl.$^5$ ................................................ B01L 3/00
[52] U.S. Cl. .................................... 422/102; 422/99; 202/168; 202/169
[58] Field of Search ..................... 422/102, 99; 203/DIG. 2; 202/169, 168; D24/8; D10/96, 101, 81; 220/661, DIG. 27

[56] References Cited

U.S. PATENT DOCUMENTS

| | | | |
|---|---|---|---|
| 440,963 | 11/1890 | Pinagel | 202/169 |
| 777,115 | 1/1904 | Lloyd | 202/69 |
| 808,997 | 1/1906 | Lloyd | 202/169 |
| 2,095,056 | 10/1937 | Clough | 422/82 |
| 2,182,564 | 12/1939 | Leiboft | 424/529 |
| 2,732,415 | 1/1956 | Klinge | 202/168 |
| 3,291,703 | 12/1966 | Dvonch et al. | 203/DIG. 2 |
| 3,527,576 | 12/1970 | Kaplan et al. | 23/299 |
| 3,803,004 | 4/1974 | Egri | 202/168 |
| 4,006,062 | 2/1977 | Bhuchar et al. | 202/169 |
| 4,255,386 | 3/1981 | Schachter et al. | 422/101 |
| 4,337,121 | 6/1982 | English | 202/69 |

FOREIGN PATENT DOCUMENTS 399293  8/1970  Fed. Rep. of Germany .

OTHER PUBLICATIONS

Catalog: *Scientific Apparatus for Environmental Testing and Drug Analysis* (1989), published by The Burkitt Group, Burkit Consultants Inc.
Catalog: *The Laboratory Catalog* (1988).

Primary Examiner—Robert J. Warden
Assistant Examiner—Laura E. Collins
Attorney, Agent, or Firm—Stephen R. Christian; Alfred L. Michaelsen

[57] ABSTRACT

The invention relates generally to laboratory glassware apparatus and particularly to laboratory apparatus and kits thereof. The disclosed apparatus is used to extract and/or concentrate specific substances for analytical purposes from sample liquids by passing a predetermined solvent through the sample. The invention includes a modular sample container body for holding a sample to be processed. The container body has a variety of disconnect joints for receiving a variety of disconnectable attachments that are used in the extraction and/or concentration process of the specific substance. The invention also includes a universal modular container body having a variety of disconnect joints that may be used with solvents having a density lesser or greater than the density of the sample liquid being processed.

23 Claims, 7 Drawing Sheets (PRIOR ART)
Fig. 1A (PRIOR ART)
Fig. 1B (PRIOR ART)
Fig. 2

MODULAR SOLVENT EXTRACTOR/CONCENTRATOR APPARATUS

FIELD OF THE INVENTION

This invention relates generally to the field of chemical laboratory glassware and particularly to laboratory apparatus employing a solvent to extract a substance from a sample and/or laboratory apparatus to increase the concentration of the substance in the solvent previously passed through the sample.

BACKGROUND OF THE INVENTION

Historically, extraction and concentration of substances from test samples, such as environmental pollutants in water and drug related substances in blood serum, are carried out in either a separate extraction apparatus and a separate concentration apparatus, or in a combined extractor/concentrator apparatus.

As is well known in the art, extraction is conducted by passing a suitable solvent through a test sample in order for the solvent to combine with any subject substance that may be present within the sample. After the sample has been adequately exposed to the solvent, the substance carrying solvent is then transferred to a separate concentrator for distillation of the solvent thereby leaving behind a concentration of the substance being sought. If a combination extractor/concentrator apparatus is being used, a valve usually located along the extract connecting tube is closed after the sample has been adequately exposed to the solvent and the substance carrying solvent has passed to the concentrator. The concentration of the substance is then increased by distilling the solvent, thereby leaving behind a concentrated solution of the subject substance.

The particular apparatus used, regardless of whether a separate extractor and concentrator or a combination thereof is used, will also depend upon the relative densities of the solvent and the sample. This is because the solvent must be introduced to the sample from above or below the contained sample depending on the relative densities of the sample and the solvent being used, in order for the solvent to pass through the sample via gravitational forces. Therefore, care must be taken to introduce the proper amount of sample and solvent into the apparatus, so that the sample and the solvent can be processed accordingly. Additionally, the apparatus must also be designed to prevent the solvent and/or the sample from back flowing through the apparatus due to head pressures.

Figure 1A:
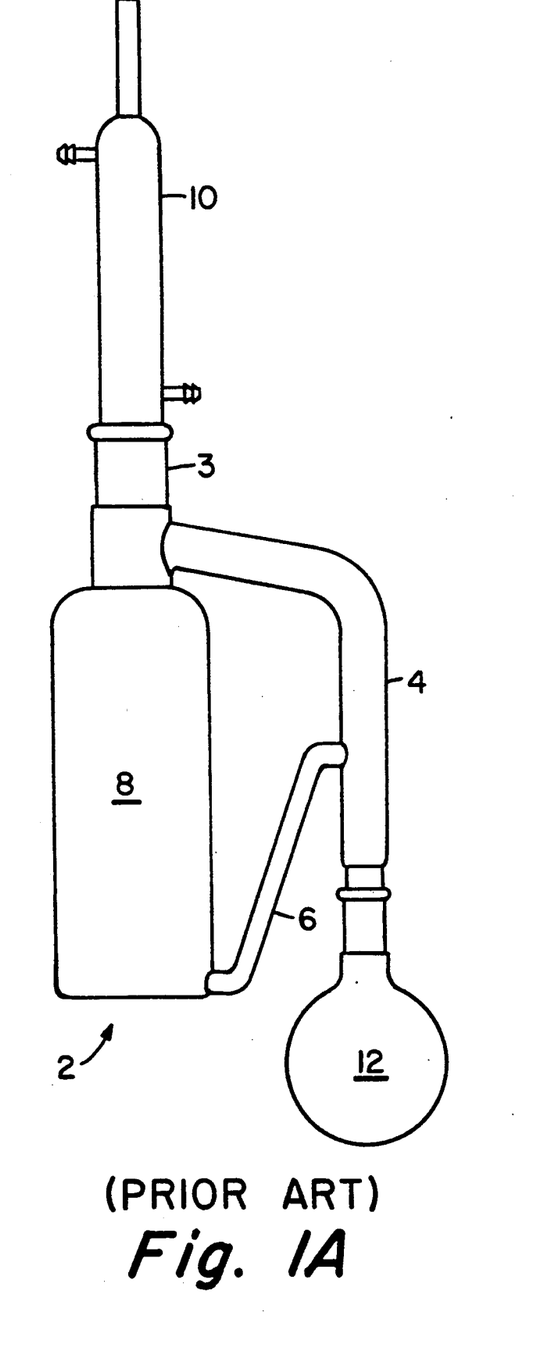
FIG. 1A is a front view of a prior art extractor apparatus.
Figure 1B:
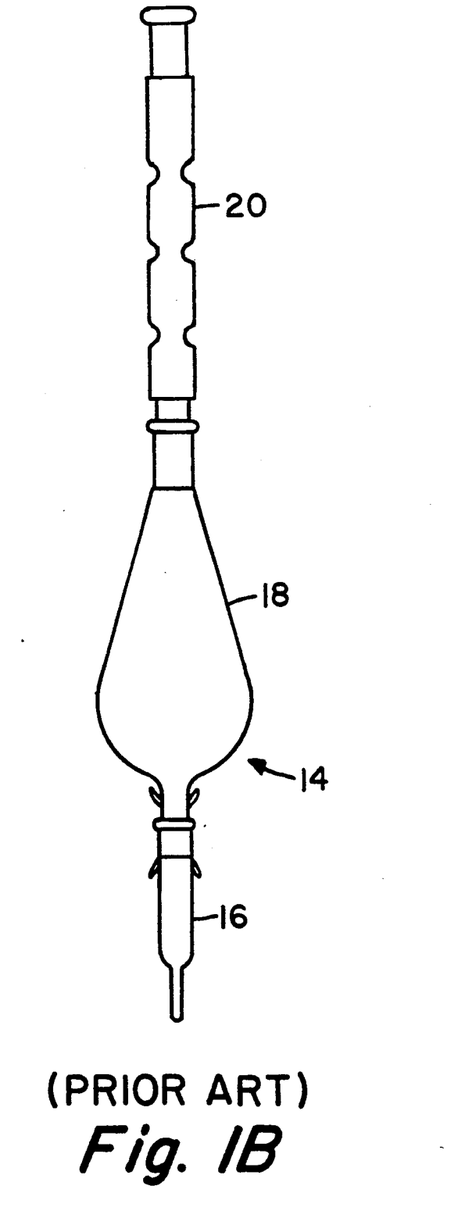
FIG. 1B is a front view of a prior art concentrator apparatus.

Representative prior art of a separate extractor for use with solvent that is of greater density than the sample and a separate concentrator are shown in FIGS. 1A and 1B respectively.

Figure 2:
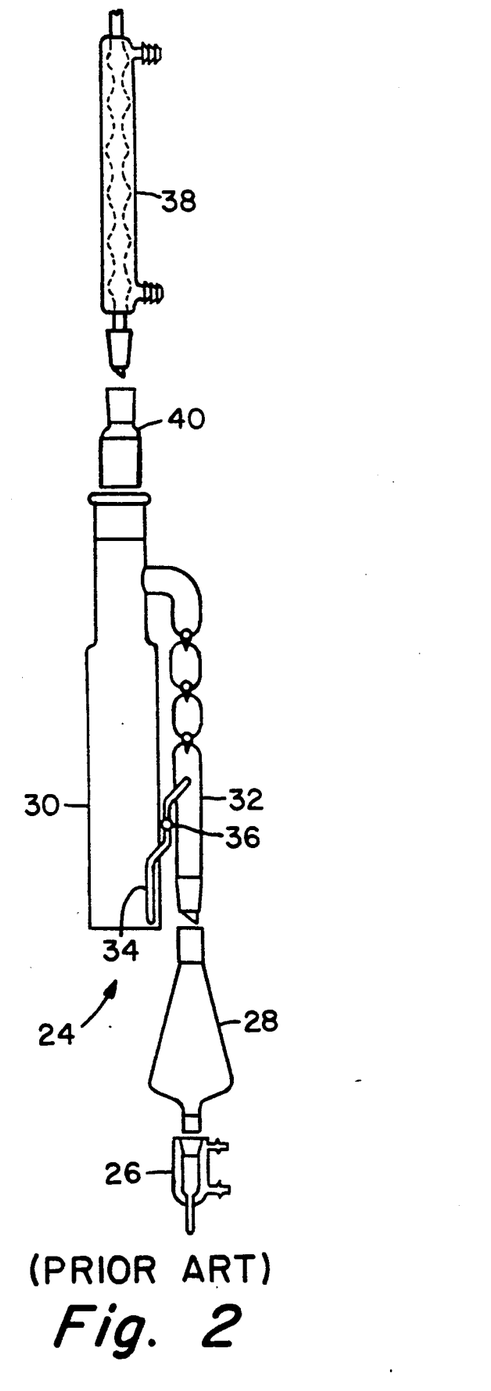
FIG. 2 is an exploded front view of a prior art combination extractor/concentrator apparatus for use with solvent having a density greater than the sample to be processed.

Representative prior art of a combined extractor/concentrator apparatus for use with a solvent that is of greater density than the sample is shown in FIG. 2.

Figure 3:
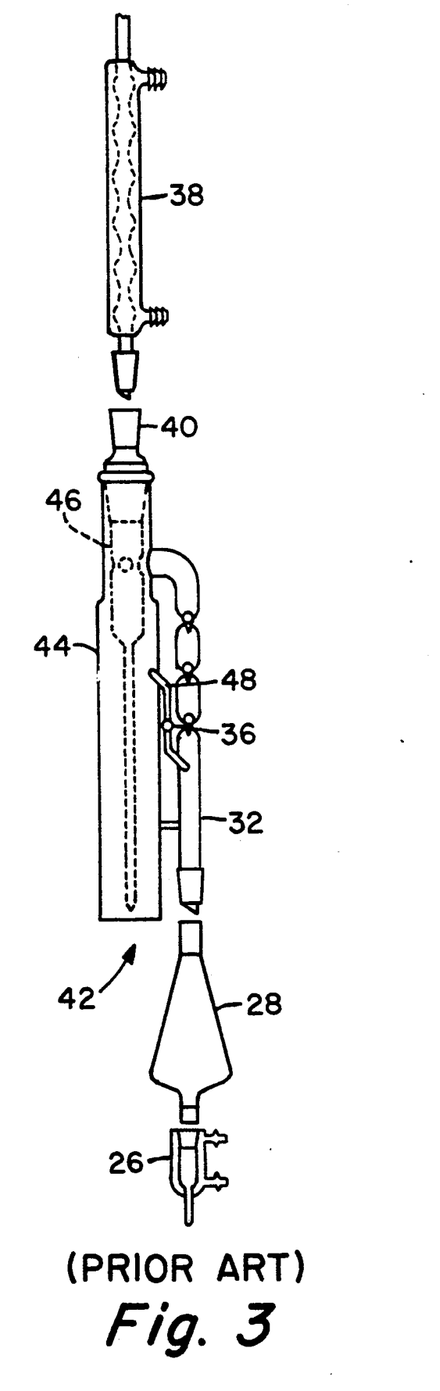
FIG. 3 is an exploded front view of a prior art combination extractor/concentrator apparatus for use with solvent having a density lesser than the sample to be processed.

Representative prior art of a combined extractor/concentrator apparatus for use with a solvent that is of lesser density than the sample is shown in FIG. 3.

Prior art apparatus typically use permanent connecting arms and connecting tubing, also referred to as cross over arms and siphon tubing, which serve to fluidly connect a portion of the apparatus to another portion of the apparatus. A shortcoming with such prior art connecting members is that they can be difficult to clean, especially if they are of a serpentine nature. Cleaning difficulties not only increases labor costs, but an improperly cleaned tubing increases the chances of contaminating samples that are to undergo processing with previously processed samples and/or solvent remaining within the tubing.

An additional shortcoming with prior art apparatus is the fragile, breakage prone nature of the apparatus due to the connecting arms and tubing being fused, or otherwise permanently attached, to the appropriate portions of the apparatus. Furthermore, repair of damaged tubing can be expensive and if the damaged tubing can not be repaired economically or promptly, the entire portion of the affected apparatus must be replaced.

Another shortcoming with prior art apparatus is a specifically designed apparatus must be used with solvents having a density greater than the sample to be processed. Conversely, a specifically designed apparatus must be used with solvents having a density lesser than the sample to be processed.

OBJECTS OF THE INVENTION

It is an object of this invention to provide extractor apparatus and combined extractor/concentrator apparatus that are easy to clean, thereby reducing the chances of contaminating subsequently processed samples and to reduce labor costs.

Another object of this invention is to provide extractor apparatus and combined extractor/concentrator apparatus with connecting means that are less fragile than connecting means employed in previous apparatus.

Another object of this invention is to provide extractor apparatus and combined extractor/concentrator apparatus that can be economically and quickly repaired, should the connecting members described above be damaged.

Yet another object of this invention is to provide an extractor body and combined extractor/concentrator body that is suitable for use with solvents having densities lesser or greater than the sample to be processed, thereby reducing the quantity of glassware to be purchased by laboratories and thereby reducing the amount of work area occupied by glassware.

A further object of this invention is to provide an extractor apparatus and combined extractor/concentrator apparatus that is compatible with conventional and common laboratory glassware such as Allihn condensers, Kuderna-Danish flasks, concentrators, and boiling flasks.

SUMMARY OF THE INVENTION

The above objects are achieved by providing apparatus and kits for a modular solvent extractor, a modular combination solvent extractor/concentrator, and a universal modular sample containing body suitable for use with the preceding, each of which are capable of accommodating a variety of disconnectable attachments.

More specifically the invention includes a modular container body for holding a sample to be treated with solvent to render an extraction therefrom having a mouth, at least one solvent vapor port, at least one solvent extract port, and at least one of the ports having disconnect means to accommodate a variety of disconnectable attachments. A hollow vapor connecting arm having a disconnect joint at one or more ends thereof and having a solvent extract inlet port having a disconnect joint is also provided herein. The solvent extract inlet port is located at a preselected position along the vapor connecting arm. An extract connecting tube having a disconnect joint at each end thereof is disclosed. The solvent extract inlet port has means to accommodate at least one of the disconnect joints of the extract connecting tube. A removable tubular insert is also disclosed for using solvent that is of a lesser density than the density of the sample. Also disclosed are embodiments of extract connecting tubes having disconnect joints at each end thereof and extract connecting tubes additionally having a stopcock, or extract flow control valve, located at a preselected position along the connecting tube.

DETAILED DESCRIPTION OF THE DRAWINGS

FIG. 1A is representative of a prior art separate solvent extractor apparatus 2 having a mouth 3, and a plain hollow vapor connector arm 4 and an extract connecting tube 6 fused to a sample containing body 8. An Allihn condenser 10 is fitted to sample containing body 8 and a round bottom boiling flask 12 is removably fitted to vapor connector arm 4.

FIG. 1B is representative of a prior art separate concentrator apparatus 14 making use of a concentrator 16 fitted to a Kuderna-Danish flask 18 which is fitted to a Snyder distillation column 20.

To use the apparatus shown in FIGS. 1A and 1B, extraction is performed by adding a solvent followed by a sample directly through mouth 3 of sample containing body 8, or alternatively, by adding solvent and sample through condensor 10 which allows the solvent and sample to ultimately pass through mouth 3. The sample is typically an aqueous solution possibly containing a substance of interest. Extract connecting tube 6 allows the solvent to pass into boiling flask 12 where heat is applied to the bottom of the flask to begin the extraction process. By adding sufficient heat to flask 12, the solvent boils and the solvent vapor travels through vapor connector arm 4 and upward through mouth 3 to condensor 10 where the solvent vapor condenses and falls back into sample containing body 8. The solvent passes through the sample repeatably for a predetermined amount of time, or until a sufficient amount of the sought after substance has been extracted from the sample and retained within the solvent. The substance bearing solvent residing in flask 12 is then transferred to flask 18 of concentrator apparatus 14. Heat is then applied to concentrator 16, usually by immersion in hot water, or alternatively, by passing hot water through a jacketed concentrator (not shown in FIG. 1B). The heat from the hot water causes the solvent to vaporize and become distilled by the solvent vapor passing through Snyder distillation column 20. Distillation is continued until there is a small volume of solvent containing a high concentration of substance remaining in concentrator 16. Thereafter, the concentrated substance can be further examined and analyzed if desired.

FIG. 2 is representative of a prior art combined solvent extractor/concentrator apparatus 24 for use with a solvent having a density greater than the density of the sample to processed. Extractor/concentrator 24 makes use of a concentrator 26 fitted to a Kuderna-Danish flask 28. A sample containing body 30 having a fused on vapor connector arm 32 and a fused on extract connecting tube 34 is shown. A stopcock 36 is located on extract connecting tube 34 for controlling the flow of solvent extract. Kuderna-Danish flask 28 is fitted to vapor connector arm 32 and Allihn condensor 38 is fitted to adaptor 40 which in turn is fitted to sample containing body 30.

Apparatus 24 is used much the same way as previously described apparatus 2 and 14, with the exception that it is not necessary to transfer the substance bearing solvent to a separate concentrator apparatus. The sample is exposed to the solvent as in apparatus 2 shown in FIG. 1A, however the solvent is heated in concentrator 26, shown in FIG. 2, during the extraction process, instead of round boiling flask 12, shown in FIG. 1A. After the extraction process has been completed, stopcock 36 on extract connecting tube 34 is closed, and the substance bearing solvent is then concentrated as previously described with respect to apparatus 14 shown in FIG. 1B. Concentrator 26 in FIG. 2 is a jacketed concentrator allowing hot water to be pumped through the concentrator for heating the solvent, and is an interchangeable alternative to immersion style concentrator 16, shown in FIG. 1B.

FIG. 3 is representative prior art of a combined solvent extractor/concentrator apparatus 42 for use with solvent having a density less than the density of the sample to be processed. Apparatus 42 generally makes use of the same elements as apparatus 24 with the exception of insert 46 being used to introduce solvent near or at the bottom of sample containing body 44, and extract connecting tube 48 being located at a higher point along the sample containing body 44 than extract connecting tube 34 of apparatus 24.

Extractor/concentrator apparatus 42 is used much the same way as apparatus 24 discussed previously and shown in FIG. 2. However, with apparatus 42, the sample to be processed is first introduced into container 44 and solvent is introduced and passed through the sample thereafter through insert 46. Sample level is more critical in apparatus 42 because the sample level must be at a point sufficiently high to allow the solvent to rise upward through the sample and pass through extract connecting tube 48, eventually finding its way into flask 28 and concentrator 26.

Figure 4:
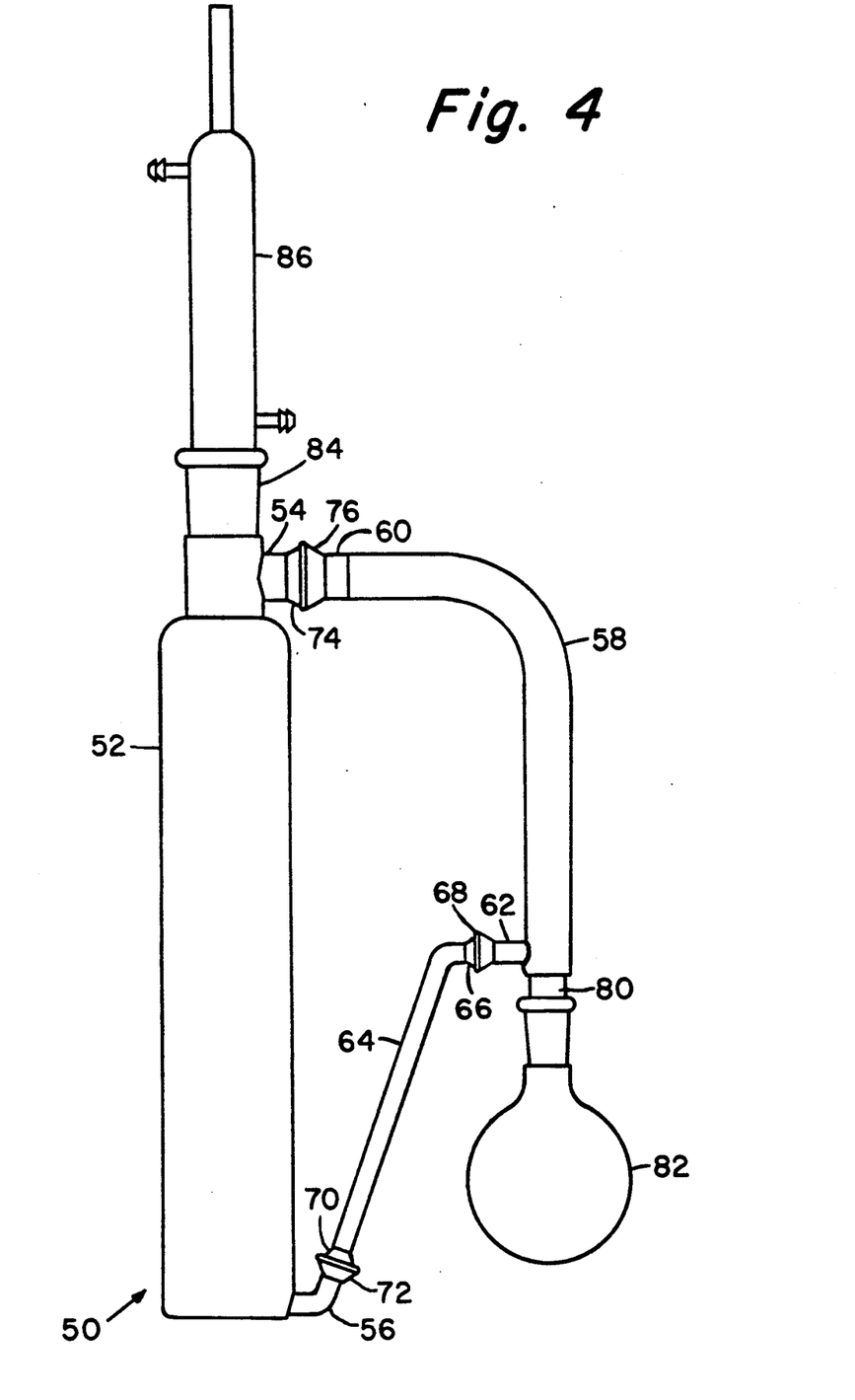
FIG. 4 is a front view of a modular extractor for use with solvent having a density greater than the sample to be processed.

FIG. 4 reveals the present invention embodied in a modular solvent extractor apparatus 50 for use with solvent having a density greater than the sample to be processed. Container body 52 makes use of a vapor inlet port 54 for allowing solvent vapor to be introduced into the upper portion of container body 52 during the extraction process. Container body 52 also makes use of an extract outlet port 56 located at a lower portion of container body 52 for allowing solvent to pass out of the container body 52 during the extraction process. Hollow connecting arm 58 is provided with an outlet 60 for allowing vapor to be returned to container body 52 via inlet port 54. Vapor connecting arm 58 is shown as having an extract inlet port 62 located at a preselected position on vapor connecting arm 58. The particular positioning of extract inlet port 62 is preferably near the lower portion of connecting arm 58. Extract connecting tube 64 is provided with disconnect joints 66 and 70 at respective ends of extract connecting tube 64. Disconnect joint 66 is accommodated by compatible disconnect joint 68 located at extract inlet port 62. Disconnect joint 70 accommodates compatible disconnect joint 72 located at extract outlet port 56. Vapor inlet port 54 also makes use of a disconnect joint 74 which accommodates and is compatible with disconnect joint 76 located at vapor outlet 60 of vapor connecting arm 58.

Disconnect joints 66–68, 70–72, and 74–76 allow for solvent extract or solvent vapor to travel through extract connecting tube 64 and vapor connecting arm 58, while additionally providing means for easily connecting and disconnecting extract connecting tube 64 and vapor connecting arm 58 from container body 52 for cleaning, repairing, switching or replacement purposes. The embodiment of the invention shown in FIG. 4 shows disconnect joints 66, 70, and 74 as being a standard ball joint design. Disconnect joints 68, 72, and 76 are shown as being a compatible socket joint design to fittingly accommodate the respective ball joints. The ball and socket joints are secured to together by standard removable metal or plastic clips that are commonly used within the field of art (not shown). The disconnect joints shown in FIG. 4 need not be of a ball and socket arrangement, as any suitable disconnectable joint design will suffice in achieving the desired results.

Vapor connecting arm end 80 is usually fitted to a round bottom boiling flask 82 by way of compatible tapered joints commonly used within the labware field. Mouth 84, located at the upper most portion of container body 52, is likewise shaped and dimensioned to accommodate desired labware having standard tapered joints such as Allihn condenser 86 fitted to mouth 84.

Figure 5:
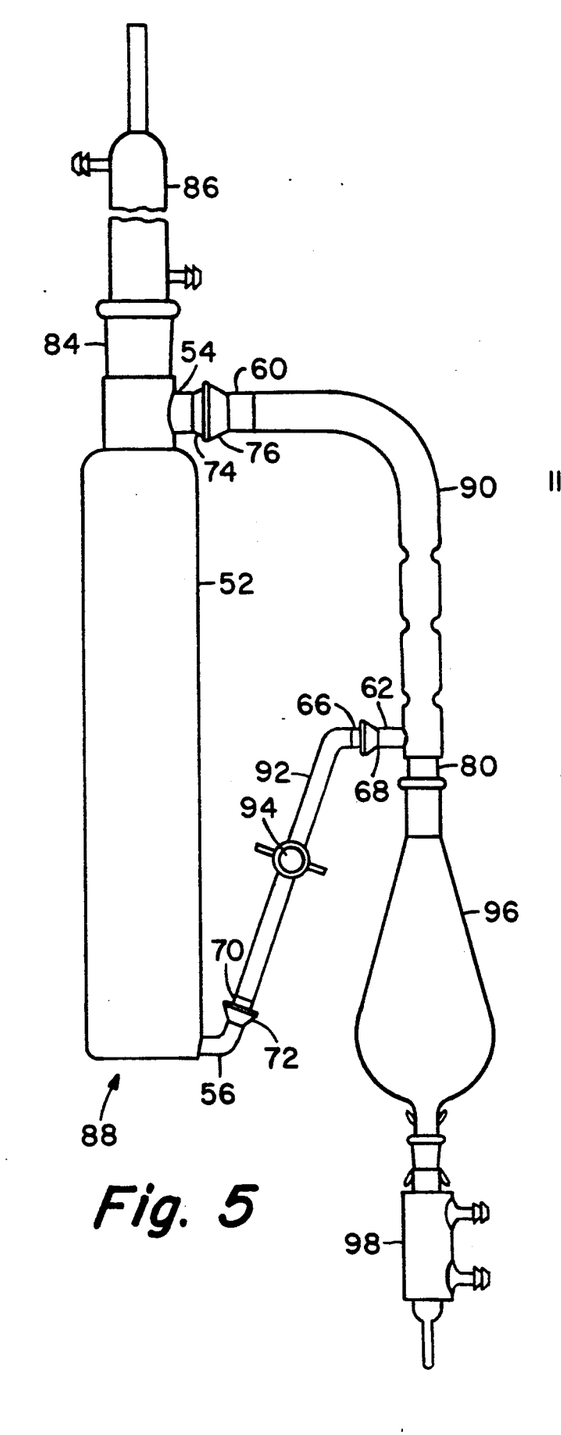
FIG. 5 is a front view of a modular combination extractor/concentrator for use with solvent having a density greater than the sample to be processed.

FIG. 5 illustrates a combined solvent extractor/concentrator apparatus embodying the present invention. Extractor/concentrator 88 is suitable for use with solvent having a greater density than the sample to be processed and has many of the same features as extractor apparatus 50 shown in FIG. 3 with the exception of the following. Modular extractor/concentrator 88 utilizes an extract connecting tube 92 which includes a stopcock or valve 94 for terminating the flow of solvent extract after the sample has been adequately exposed to the solvent. Vapor connecting arm 90 incorporates a distillation column within connecting arm 90, however a separate distillation column with suitable connecting tubes and connectors could be used in lieu thereof. Extractor/concentrator apparatus 88 differs from extractor 50 in that a Kuderna-Danish flask 96 is fitted to vapor connecting arm end 80 instead of boiling flask 82 in extractor 50, and concentrator 98 is fitted to Kuderna-Danish flask 96.

Disconnect joints 66–68, 70–72, and 74–76 are employed in extractor/concentrator apparatus 88 for the same reasons as set forth in the discussion of extractor 50 above.

Figure 6:
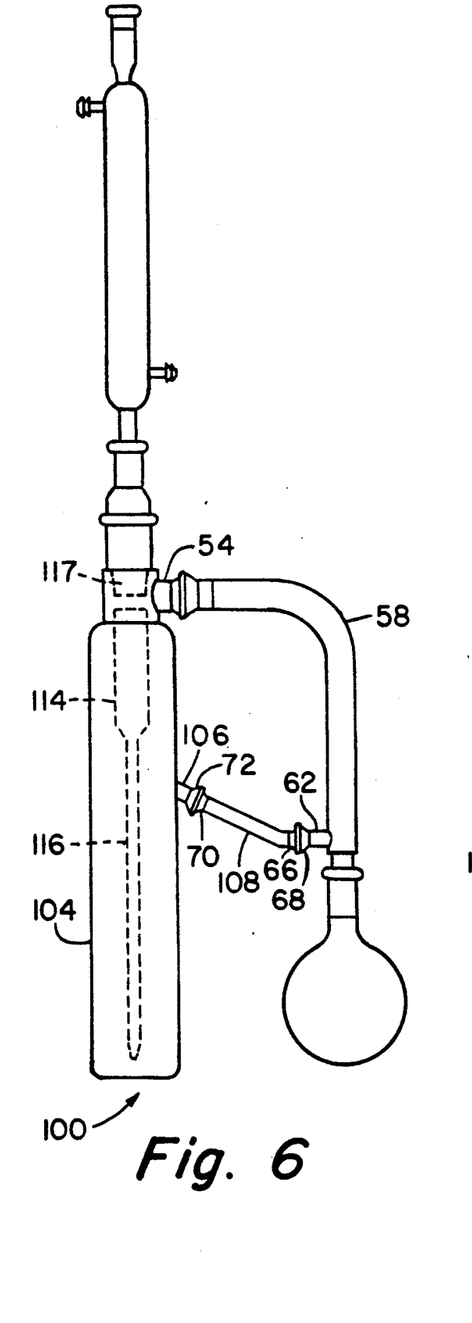
FIG. 6 is a front view of a modular extractor for use with solvent having a density less than the sample to be processed.
Figure 7:
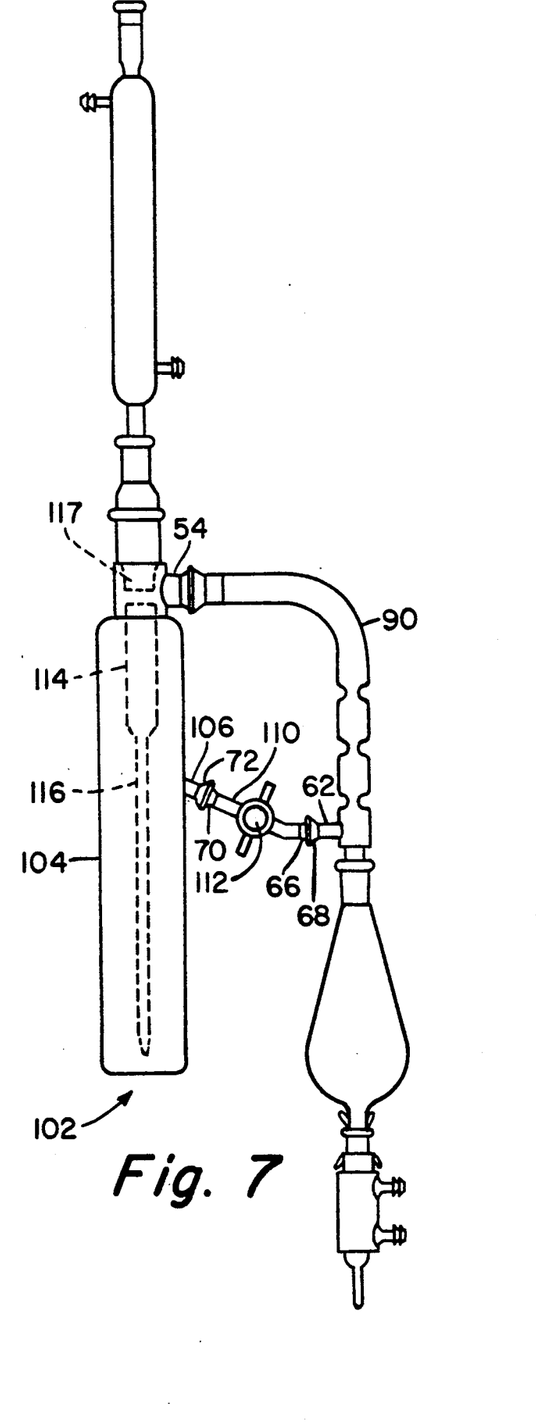
FIG. 7 is a front view of a modular combination extractor/concentrator for use with solvent having a density less than the sample to be processed.

FIG. 6 and FIG. 7 reveal a modular extractor 100 and a modular combined extractor/concentrator 102 respectively, both of which embody the present invention. Both modular extractor 100 and modular extractor/concentrator 102 are suitable for use with solvents having a density less than the sample to be processed.

Container body 104 as shown in FIGS. 6 and 7 makes use of an extract port 106 positioned at a point between the middle and upper portion of container body 104. Such positioning allows solvent to siphon out of container body 104, yet allows for the retention of the sample, provided container body 104 is filled to an appropriate level with the sample to be processed.

Modular extractor apparatus 100 employs an extract connecting tube 108 and modular combination extractor/concentrator apparatus 102 employs an extract connecting tube 110, both of which have upon either end thereof disconnect joints 66 and 70 which are accommodated by compatible disconnect joints 68 and 72 located at extract outlet port 106 and extract inlet port 62 respectively. The disconnect joints shown in FIGS. 6 and 7 are of a ball and socket design and have the same advantages as discussed earlier with respect to extractor apparatus 50. Connecting tube 110 of modular combination extractor/concentrator 102, makes use of a stopcock or valve 112 in order to allow for the concentration of the extract.

In order to use solvent having a density less than the sample to be processed, the solvent must be introduced at an acceptable level within container body 104 to allow the solvent to rise upward through the sample. This is accomplished by using a tubular insert 114 in both modular extractor 100 and modular combination extractor/concentrator 102. Insert 114 allows solvent to pass through axial passage 116 while also allowing solvent vapor to flow back into container body 104 via vapor inlet port 54 and perpendicular passage 117 which adjoins axial passage 116. Tubular insert 114 is easily inserted and removed from container body 104 for cleaning, repair, or replacement.

Figure 8:
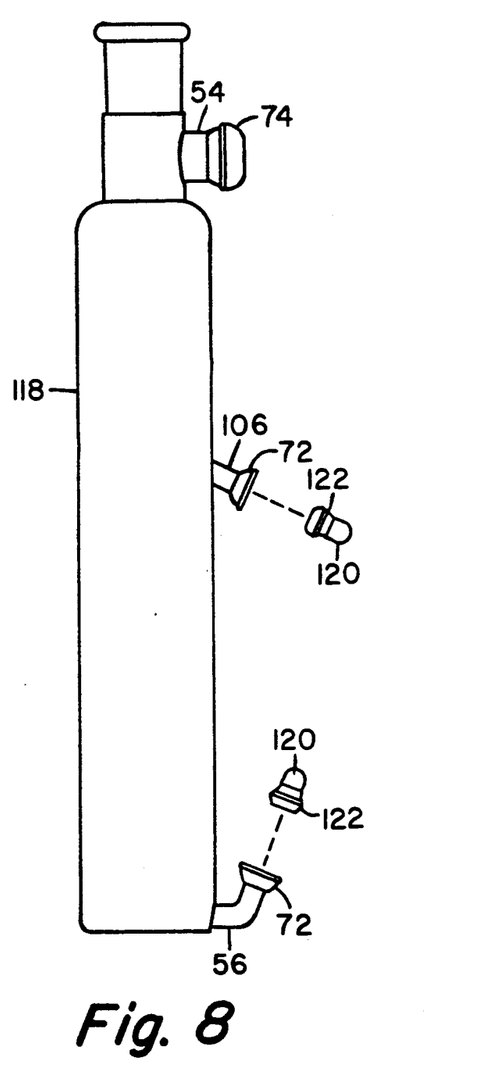
FIG. 8 is a front view of a universal modular body for use with solvent having a density less or greater than the sample to be processed.
Figure 9:
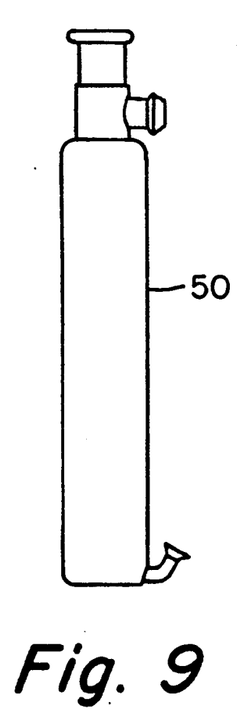
FIG. 9 is a front view of a modular sample containing body for use with solvent having a density greater than the sample to be processed.
Figure 10A:
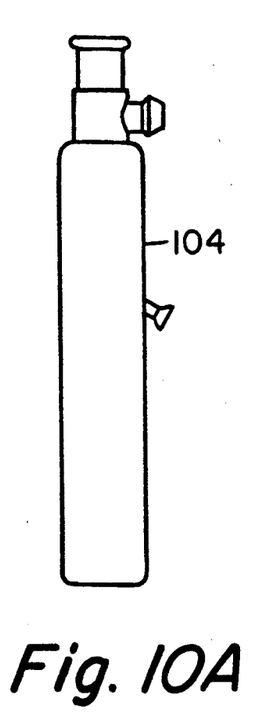
FIG. 10A is a front view of a modular sample containing body for use with solvent having a density less than the sample to be processed.
Figure 10B:
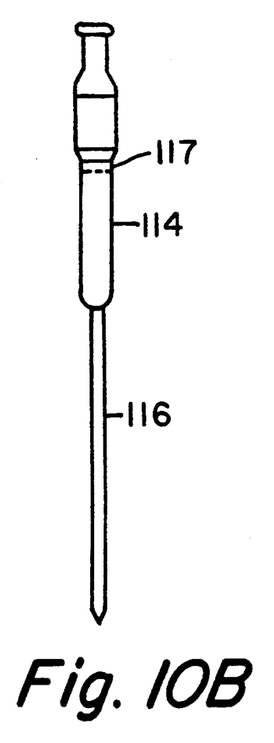
FIG. 10B is a front view of a modular insert for use with either a modular body or a universal modular body in which a solvent having a density less than the sample is to be processed.

A universal modular container body 118, which is suitable for use with solvents having a density lesser or greater than the density of the sample to be processed, is revealed in FIG. 8. Additionally, universal modular container body 118 is suitable for use within an extractor apparatus or within a combination extractor/concentrator apparatus, regardless of solvent density.

Universal modular solvent body 118 makes use of a vapor inlet port 54, extract port 56, and extract port 106. Each port makes use of disconnect joints, such as ball joint 74 at the end of vapor inlet port 54 and socket joint 72 at the end of extract ports 56 and 106. As mentioned earlier, a ball and socket disconnect joint is the preferred disconnect joint, but any suitable disconnect joint will accomplish the desired results, for example joints which make use of compressible O-rings may be utilized.

Disconnect joint plug 120, having a compatible disconnect joint 122, used to seal an unused port, allows universal modular container body 118 to be used to form an apparatus suitable for a number of solvents and samples. Thus, the embodiment of modular universal container body 118 shown in FIG. 8 allows for the purchasing of a single container that can be used with or without tubular insert 114 and can be used with a variety of connecting tubing and arms, instead of purchasing several container bodies having tubing that are specially designed for use with certain solvent densities and processes. The universal modular container body also provides an economical spare container body because it can be used to replace a damaged container body within an apparatus using a solvent having density greater, or lesser, than the sample to be processed.

Figure 11A:
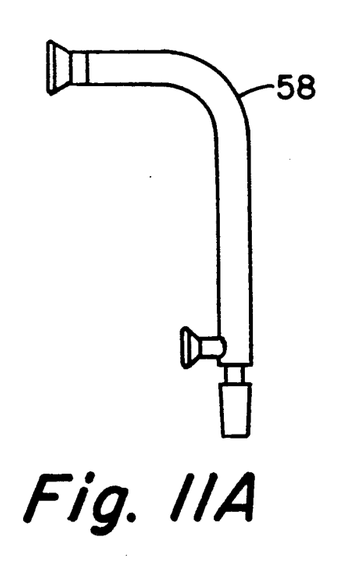
FIG. 11A is a front view of a plain hollow solvent vapor connecting arm.
Figure 11B:
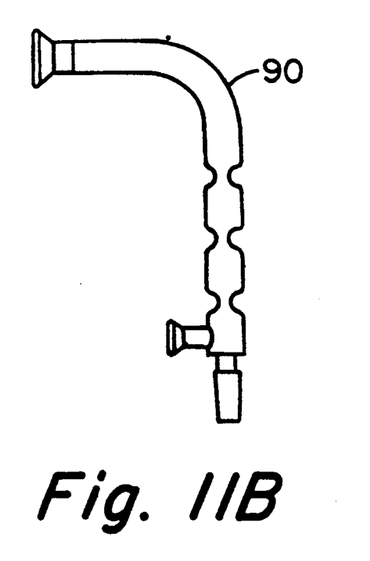
FIG. 11B is a front view of a hollow solvent vapor connecting arm incorporating a Snyder distillation column therein.

Isolated views of embodiments of container bodies 52 and 104, tubular insert 114, and various embodiments of disconnectable attachments are shown in FIGS. 9, 10A, 10B, and 12A-E respectively, in order to better illustrate the modular characteristic of the invention. Isolated views of vapor connecting arms 58 and 90, which are particularly suitable for use in practicing the present invention, are shown in FIGS. 11A and 11B.

Isolated views of preferred embodiments of disconnectable attachments that are suitable for practicing the present invention are shown in FIGS. 12A through 12E. The disconnectable attachments are interchangeable among themselves and are particularly suitable for use with the embodiments of the various container bodies described herein. It should be noted, although it will be apparent to those skilled in the relevant art, that the embodiments of the container bodies and various disconnectable attachments must be combined with standard laboratory glassware readily available from glassware suppliers in order to form complete apparatus, such as the apparatus illustrated and discussed herein.

Figure 12A:
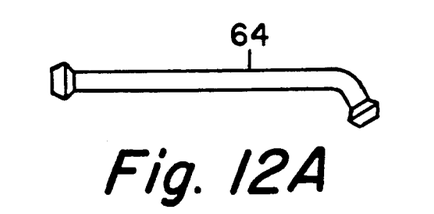
FIGS. 12A through 12E are front views of a variety of solvent extract connecting tubes.
Figure 12B:
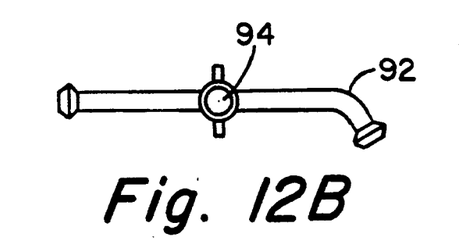

Isolated views of embodiments of extract connecting tube 64 and extract connecting tube 92 having a stopcock 94 are shown in FIGS. 12A and 12B.

Figure 12C:
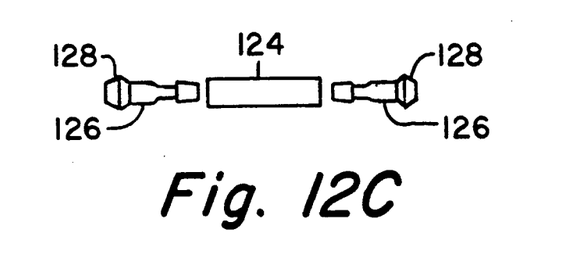

An alternative connecting means in lieu of, for example, tube 64 (FIG. 4) or 108 (FIG. 6) is shown in FIG. 12C. Flexible hose 124 is sized to be attached to tubulations 126 having disconnect joints 128. Flexible hose 124 may be attached to tubulations 126 by standard clamps well known and used within the field of art.

Figure 12D:
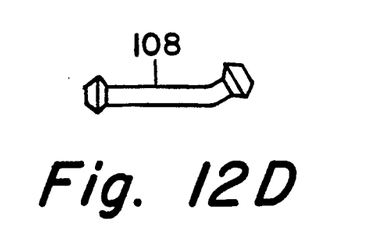
Figure 12E:
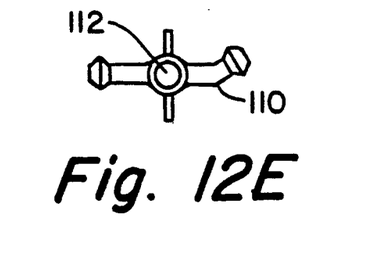

Isolated views of extract connecting tube 108 and extract connecting tube 110 having a stopcock 112 are shown in FIGS. 12D and 12E respectively.

As can be seen in the isolated views shown in FIGS. 9 through 12, a chosen container body and selected individual attachments are particularly suited to being used and marketed as a kit. For example, a kit for use in connection with standard laboratory glassware to form a complete apparatus may be formed by including within the kit a container body 50, a vapor connecting arm 90, and a extract connecting tube 92. The remaining standard laboratory components such as an Allihn condensor, concentrator, a Kuderna-Danish flask, and a number of disconnect joint clips needed to complete the apparatus could also be provided within the kit if so desired.

Although the present invention has been shown and described with respect to detailed embodiments thereof, it will be understood by those skilled in the art that various changes in the form and detail thereof may be made without departing from the spirit and scope of this invention.

I claim:

1. A kit for forming a modular solvent extractor apparatus comprising:
    a) a container body for holding a sample to be treated with a solvent to render an extraction therefrom, the container body having a mouth, at least one solvent vapor port, and at least one solvent extract port;
    b) an extract connecting tube having a disconnect joint at each end thereof;
    c) a hollow vapor connecting arm having a disconnect joint at one or both ends thereof, a solvent extract inlet port being located at a preselected position along the vapor arm and having a disconnect joint to accommodate one of the disconnect joints of the extract connecting tube;
    d) a disconnect joint at the solvent vapor port to accommodate one of the disconnect joints of the vapor connecting arm; and
    e) a disconnect joint the at least one solvent extract port to accommodate one of the disconnect joints of at least one the extract connecting tube.

2. The extractor kit of claim 1 wherein at least one of the disconnect joints comprises a socket joint accommodating a ball joint thereby forming a ball and socket joint arrangement.

3. A kit for forming a modular solvent extractor apparatus comprising:
    a) a container body for holding a sample to be treated with solvent to render an extraction therefrom, the container body having a mouth, at least one solvent vapor port, and at least one solvent extract port;
    b) an extract connecting tube having a disconnect joint at each end thereof;
    c) a hollow vapor connecting arm having a disconnect joint at one or both ends thereof, a solvent extract inlet port having a disconnect joint to accommodate one of the disconnect joints of the extract connecting tube, and the solvent extract inlet port being located at a preselected position along the vapor arm;
    d) a disconnect joint at the solvent vapor port to accommodate at least one of the disconnect joints of the vapor connecting arm;
    e) a disconnect joint at the solvent extract port to accommodate one of the disconnect joints of the extract connecting tube there by allowing the container body to be connected to the vapor arm by the extract connecting tube; and
    f) a removable tubular insert for placement within the container body, the insert having a passage extending axially therethrough, an adjoining through passage extending generally perpendicularly from the axially extending passage, and the insert being shaped and sized to be accommodated by the mouth of the container body.

4. The extractor kit of claim 3 wherein at least one of the disconnect joints comprises a socket joint accommodating a ball joint thereby forming a ball and socket joint arrangement.

5. A kit for forming a modular combination solvent extractor/concentrator comprising:
   a) a container body for holding a sample to be treated with solvent to render an extraction therefrom, the container body having a mouth, at least one solvent vapor port, and at least one solvent extract port;
   b) an extract connecting tube having a disconnect joint at each end thereof and a stopcock located at a predetermined position along the extract connecting tube;
   c) a hollow vapor connecting arm having a disconnect joint at one or both ends thereof, a solvent extract inlet port being located at a preselected position along the vapor arm and having a disconnect joint to accommodate one of the disconnect joints of the extract connecting tube;
   d) a disconnect joint at the solvent vapor inlet port to accommodate one of the disconnect joints of the vapor connecting arm; and
   e) a disconnect joint at the solvent extract port to accommodate one of the disconnect joints of the extract connecting tube.

6. The extractor/concentrator kit of claim 5 wherein at least one of the disconnect joints comprises a socket joint accommodating a ball joint thereby forming a ball and socket joint arrangement.

7. The extractor/concentrator kit of claim 5 wherein the vapor connecting arm comprises a Snyder distillation column therein.

8. A kit for forming a modular combination solvent extractor/concentrator comprising:
   a) a container body for holding a sample to be treated with solvent to render an extraction therefrom, the container body having a mouth, at least one solvent vapor port, and at least one solvent extract port;
   b) an extract connecting tube having a disconnect joint at each end thereof and a stopcock located at a predetermined position along the extract connecting tube;
   c) a hollow vapor connecting arm having a disconnect joint at one or more ends thereof, a solvent extract inlet port being located at a preselected position along the vapor arm and having a disconnect joint to accommodate one of the disconnect joints of the extract connecting tube, and the extract inlet port;
   d) a disconnect joint at the solvent vapor port to accommodate one of the disconnect joints of the vapor connecting arm;
   e) a disconnect joint at the solvent extract port to accommodate one of the disconnect joints of the extract connecting tube thereby allowing the container body to be connected to the vapor arm by the extract connecting tube; and
   f) a removable tubular insert for placement within the container body, the insert having a passage extending axially therethrough, an adjoining through passage extending generally perpendicularly from the axially extending passage, and the insert being shaped and sized to be accommodated by the mouth of the container body.

9. The extractor/concentrator kit of claim 8 wherein at least one of the disconnect joints comprises a socket joint accommodating a ball joint thereby forming a ball and socket joint arrangement.

10. The extractor/concentrator kit of claim 8 wherein the vapor connecting arm comprises a Snyder distillation column therein.

11. A modular solvent extractor apparatus comprising:
   a) a container body for holding a sample to be treated with a solvent to render an extraction therefrom, the container body having a mouth, at least one solvent vapor port having a disconnect joint, and at least one solvent extract port being located at a preselected position upon the container body having a disconnect joint;
   b) an extract connecting tube having a disconnect joint at each end thereof, one of the disconnect joints being accommodated by the joint on the solvent extract port;
   c) a hollow vapor connecting arm having a disconnect joint at both ends thereof, one of the disconnect joints accommodating the joint means at the solvent vapor port; and
   d) a solvent extract inlet port being located at a preselected position along the vapor arm and having a disconnect joint accommodating the remaining disconnect joint of the extract connecting tube.

12. The apparatus of claim 11 wherein at least one of the disconnect joints comprises a socket joint accommodating a ball joint thereby forming a ball and socket joint arrangement.

13. The apparatus of claim 11 further comprising the sample containing body having at least one solvent extract port having a disconnect joint accommodating a disconnect joint plug.

14. The modular solvent extractor apparatus of claim 11 further comprising:
   a) a Kuderna-Danish flask having a first disconnect joint and a second disconnect joint, the first disconnect joint being connectable to one of the disconnect joints located at one of the ends of the vapor connecting arm; and
   b) a concentrator tube having a disconnect joint which is connectable to the second disconnect joint of the Kuderna-Danish flask; and
   c) a condensor having a disconnect joint which is connectable to the mouth of the container body.

15. A modular combination solvent extractor/concentrator apparatus comprising:
   a) a container body for holding a sample to be treated with a solvent to render an extraction therefrom, the container body having a mouth, at least one solvent vapor port having a disconnect joint, and at least one solvent extract port being located at a preselected position upon the container body having a disconnect joint;
   b) an extract connecting tube having a stopcock located at a preselected position along the extract connecting tube and a disconnect joint at each end of the extract connecting tube, one of the disconnect joints being accommodated by the disconnect joint on the solvent extract port;
   c) a hollow vapor connecting arm having a disconnect joint at both ends, one of the disconnect joints accommodating the disconnect joint at the solvent vapor port;

d) a Snyder distillation column within the vapor connecting arm; and e) a solvent extract inlet port being located at a preselected position along the vapor arm and having a disconnect joint accommodating the remaining disconnect joint of the extract connecting tube.

16. The modular combination solvent extractor/concentration apparatus of claim 15 further comprising:

a) a Kuderna-Danish flask having a first disconnect joint and a second disconnect joint, the first disconnect joint being connectable to one of the disconnect joints located at one of the ends of the vapor connecting arm; and b) a concentrator tube having a disconnect joint which is connectable to the second disconnect joint of the Kuderna-Danish flask; and c) a condenser having a disconnect joint which is connectable to the mouth of the container body.

17. The apparatus of claim 15 wherein at least one of the disconnect joints comprises a socket joint accommodating a ball joint thereby forming a ball and socket joint arrangement.

18. The apparatus of claim 15, further comprising the sample containing body having at least one solvent extract port having a disconnect joint accommodating a disconnect joint plug.

19. An apparatus as claimed in claim 15, comprising a removable tubular insert for placement within the container body, the insert having a passage extending axially therethrough for introducing solvent at a level below the middle portion of the container body, an adjoining through passage extending generally perpendicularly from the axially extending passage, and the insert being shaped and sized to be accommodated by the mouth of the container body.

20. A container body for holding a sample to be treated with solvent to render an extraction therefrom comprising:

a) an upper portion, a middle portion, and a lower portion;

b) a mouth extending from the upper portion;

c) a vapor port located within the upper portion;

d) an upper extract port located with the middle portion;

e) a lower extract port located within the lower portion;

f) each of the ports having a disconnect joint to accommodate disconnectable attachments; and g) a removable tubular insert for placement within the container body, the insert having a passage extending axially therethrough for introducing solvent at a level below the middle portion of the container body, an adjoining through passage extending generally perpendicularly from the axially extending passage, and the insert being shaped and sized to be accommodated by the mouth of the container body.

21. A container body as claimed in claim 20 wherein at least one of the disconnect joints comprises a socket joint accommodating a ball joint thereby forming a ball and socket joint arrangement.

22. A container body for holding a sample to be treated with solvent to render an extraction therefrom comprising:

a) an upper portion, a middle portion, and a lower portion;

b) a mouth extending from the upper portion;

c) a vapor port located within the upper portion;

d) a solvent extract port located with the middle portion;

e) each of the ports having a disconnect joint to accommodate disconnectable attachments; and f) a removable tubular insert for placement within the container body, the insert having a passage extending axially therethrough for introducing solvent at a level below the middle portion of the container body, an adjoining through passage extending generally perpendicularly from the axially extending passage, and the insert being shaped and sized to be accommodated by the mouth of the container body.

23. A container body as claimed in claim 22 wherein at least one of the disconnect joints comprises a socket joint accommodating a ball joint thereby forming a ball and socket joint arrangement.

* * * * *

REEXAMINATION CERTIFICATE (2276th)

United States Patent [19]

Killough

[11] B1 5,098,662

[45] Certificate Issued Apr. 19, 1994

[54] MODULAR SOLVENT EXTRACTORY CONCENTRATOR APPARATUS

[75] Inventor: Bruce A. Killough, Corning, N.Y.

[73] Assignee: Corning Incorporated, Corning, N.Y.

Reexamination Request:
No. 90/002,909, Dec. 8, 1992

Reexamination Certificate for:
Patent No.: 5,098,662
Issued: Mar. 24, 1992
Appl. No.: 566,216
Filed: Aug. 10, 1990

[51] Int. Cl.⁵ .................................................. B01L 3/00
[52] U.S. Cl. .................................... 422/102; 422/99; 202/168; 202/169
[58] Field of Search ........................ 422/102, 99; 203/DIG. 2; 202/168, 169; 220/661, DIG. 27; D24/8; D10/81, 96, 101

[56] References Cited

U.S. PATENT DOCUMENTS

| | | | |
|---|---|---|---|
| 440,963 | 11/1890 | Pinagel | 202/169 |
| 777,115 | 1/1904 | Lloyd | 202/169 |
| 808,997 | 1/1906 | Lloyd | 202/169 |
| 2,095,056 | 10/1937 | Clough | 422/82 |
| 2,182,564 | 12/1939 | Leiboft | 424/529 |
| 2,732,415 | 1/1956 | Klinge | 202/168 |
| 3,291,703 | 12/1966 | Dvonch et al. | 203/DIG. 2 |
| 3,527,576 | 12/1970 | Kaplan et al. | 23/299 |
| 3,803,004 | 4/1974 | Egri | 202/168 |
| 4,006,062 | 2/1977 | Bhuchar et al. | 202/169 |
| 4,255,386 | 3/1981 | Schachter et al. | 422/101 |
| 4,337,121 | 6/1982 | English | 202/169 |

FOREIGN PATENT DOCUMENTS

399293 8/1970 Fed. Rep. of Germany.

OTHER PUBLICATIONS

Catalog: Scientific Apparatus For Environmental Testing and Drug Analysis (1989), published by the Burkitt Group, Burkitt Consultants Inc.
Catalog: *The Corning Laboratory Catalog* (1988).
*Kontes Environmental Products* catalogue of May, 1988, p. 4.
*Supelco Chromatography Supplies* catalogue 24 of 1986, p. 184.
Kontes, *Chemistry and Life Sciences Products,* 1989 catalog, p. 333.

*Primary Examiner*—James C. Housel

[57] ABSTRACT

The invention relates generally to laboratory glassware apparatus and particularly to laboratory apparatus and kits thereof. The disclosed apparatus is used to extract and/or concentrate specific substances for analytical purposes from sample liquids by passing a predetermined solvent through the sample. The invention includes a modular sample container body for holding a sample to be processed. The container body has a variety of disconnect joints for receiving a variety of disconnectable attachments that are used in the extraction and/or concentration process of the specific substance. The invention also includes a universal modular container body having a variety of disconnect joints that may be used with solvents having a density lesser or greater than the density of the sample liquid being processed.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-23 are cancelled.

* * * * *